US006437212B1

United States Patent
La Fortune

(12) United States Patent
(10) Patent No.: US 6,437,212 B1
(45) Date of Patent: Aug. 20, 2002

(54) REDUCED ODOR ABSORBENT ARTICLE AND METHOD

(75) Inventor: Jeffrey Mark La Fortune, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/698,603

(22) Filed: Oct. 27, 2000

(51) Int. Cl.$^7$ .................................................. A61F 13/15
(52) U.S. Cl. ....................... 604/359; 604/367; 604/360
(58) Field of Search ................................. 604/359, 360, 604/367, 361, 362; 424/402, 443

(56) References Cited

U.S. PATENT DOCUMENTS

| | | | | |
|---|---|---|---|---|
| 3,622,261 A | * | 11/1971 | Cotton ........................ 8/116.4 |
| 4,263,363 A | * | 4/1981 | Buck et al. .................. 428/284 |
| 4,469,635 A | * | 9/1984 | Peterson ...................... 260/403 |
| 4,673,402 A | * | 6/1987 | Weisman et al. ............ 604/368 |
| 5,424,059 A | | 6/1995 | Prencipe et al. ............... 424/52 |
| 5,531,982 A | | 7/1996 | Gaffar et al. .................. 424/49 |
| 5,560,906 A | | 10/1996 | Scodari et al. ................ 424/54 |
| 5,624,676 A | | 4/1997 | Mackey et al. .............. 424/414 |
| 5,635,191 A | * | 6/1997 | Roe et al. .................... 424/402 |
| 5,705,164 A | | 1/1998 | Mackey et al. .............. 424/400 |
| 5,728,225 A | * | 3/1998 | Duflot et al. .................. 127/29 |
| 5,801,116 A | | 9/1998 | Cottrell et al. ............... 502/404 |
| 5,919,440 A | | 7/1999 | Kaiser et al. ................ 424/76.4 |
| 5,945,110 A | | 8/1999 | Vianen et al. ............... 424/401 |
| 5,968,025 A | | 10/1999 | Roe et al. .................... 604/364 |
| 6,031,147 A | * | 2/2000 | Gross ........................... 604/359 |
| 6,074,631 A | | 6/2000 | Tsuchiya et al. ............... 424/65 |
| 6,080,391 A | * | 6/2000 | Tsuchiya et al. ............... 424/65 |
| 6,086,854 A | * | 7/2000 | Arnold ......................... 424/44 |

OTHER PUBLICATIONS

Roquette America, Inc., Chemical Product Specifications, 6 pages.

* cited by examiner

Primary Examiner—John G. Weiss
Assistant Examiner—Jacqueline Stephens
(74) Attorney, Agent, or Firm—Thomas J. Connelly; Douglas G. Glantz

(57) ABSTRACT

A novel article and method are disclosed for reducing malodor in disposable products for the absorption of body fluids. An effective amount of pentitol is applied to a disposable absorbent material, prior to its use. In one aspect, the invention provides a water-swellable, water-insoluble, hydrogel-forming polymeric absorbent material. In one aspect, the pentitol is compositionally part of the absorbent structure or is coated on the absorbent material present in the absorbent structure. The pentitol preferably is located in the area of insult, i.e., that area of the absorbent product to be exposed to the body fluid intended to be absorbed. The pentitol in the novel article and method of the present invention is effective in preventing malodor.

19 Claims, 1 Drawing Sheet

REDUCED ODOR ABSORBENT ARTICLE AND METHOD

BACKGROUND OF THE INVENTION

1. Technical Field

This invention relates to an absorbent article and method for reducing malodor in absorbents used for absorbing body fluids. In one aspect, this invention relates to a novel article for reducing malodor in disposable absorbent products and a method for forming the novel article.

2. Background

Disposable absorbent products currently find widespread use in many applications. In the infant care and child care markets, disposable diapers and training pants have replaced reusable cloth absorbent articles. Other widely successful disposable absorbent products include feminine care products such as sanitary napkins or tampons, adult incontinence products, and health care products such as surgical drapes or wound dressings.

A disposable absorbent product includes a composite structure providing a topsheet, a backsheet, and an absorbent structure between the topsheet and backsheet. The disposable absorbent products include some type of fastening system for fitting the product onto a wearer or an undergarment of the wearer.

Disposable absorbent products are subjected to one or more liquid insults, such as of water, urine, menses, or blood, during use. As such, the outer cover backsheet materials of the disposable absorbent products are made of liquid insoluble and liquid impermeable materials, such as polyolefin films, having sufficient strength and handling capabilities that the disposable absorbent product retains its integrity during use by a wearer and does not allow leakage of the liquid insulting the product.

INTRODUCTION TO THE INVENTION

Although currently available disposable baby diapers and other disposable absorbent products have been accepted by the public, these current products still have need of improvement in specific areas.

Absorbent products intended to absorb urine, for example, may have an unpleasant odor. To render the use and changing of absorbent products less objectionable, a variety of solutions reduce or mask malodors associated with used absorbent products.

One method for deodorizing diapers includes applying one or more masking agents, such as perfuming agents, to a disposable absorbent product. The perfuming agents contain chemicals which are intended to mask malodors in the used product. The use of masking agents, such as perfumes, is not entirely successful, as some individuals exhibit skin or respiratory sensitivities to such perfuming agents. The perfuming agent does not eliminate the malodors in the used absorbent products, and the odor which results from the combination of the used absorbent product and perfuming agent is not always pleasant.

Certain chemical compositions for deodorizing diapers, including acidic materials, antibacterial materials, and solvents which kill bacteria require EPA registration as a pesticide health concern.

Accordingly, there is a need for a new disposable absorbent article and method which reduce the malodors from urine in the used article.

It is an object of the present invention to provide a novel absorbent article and method capable of reducing the malodors from urine in the used article.

It is an object of the present invention to provide a novel absorbent article and method capable of reducing the malodors from body fluids in the used article.

It is another object of the present invention to provide a novel disposable absorbent article and method capable of reducing the malodors from urine in the used article in an efficient and effective manner.

It is an object of the present invention to provide a novel disposable absorbent article and method capable of reducing the malodors from urine in absorbent products using a material safe for human consumption.

It is still another object of the present invention to provide a novel disposable absorbent article and method capable of reducing the malodors from urine in absorbent products without relying completely on masking agents such as perfumes.

It is an object of the present invention to provide a novel disposable absorbent article and method capable of reducing the malodors from urine in absorbent products which is biodegradable.

These and other objects of the present invention will become apparent from a careful inspection of the detailed description and the figures of the drawings which follow.

SUMMARY OF THE INVENTION

The present invention provides an article and method for reducing malodor in disposable products for the absorption of body fluids. An effective amount of a pentitol for reducing malodor is applied to an absorbent article, prior to its use. In one aspect, an effective amount of a pentitol for reducing malodor is applied to a fibrous absorbent core in a disposable diaper, prior to its use. In one aspect, the invention provides a novel article and method including an absorbent structure and a xylitol applied to the absorbent product in an amount in the range of from about 4 to about 25 weight percent based on total weight of the absorbent core.

In one aspect, the invention provides a novel article and method including an absorbent structure having from about 10 to about 100 weight percent, based on absorbent structure weight, of a hydrogel-forming polymeric absorbent material and a pentitol applied to the absorbent product. In one aspect, the pentitol is compositionally part of the hydrogel-forming polymeric absorbent material present in the absorbent structure. In one aspect, the pentitol is coated on the hydrogel-forming polymeric absorbent material present in the absorbent structure.

In one aspect, the pentitol is positioned in the area of insult of urine on the absorbent structure.

The pentitol in the novel article and method of the present invention is effective in reducing malodor from urine in the used article.

DETAILED DESCRIPTION

Figure 1:
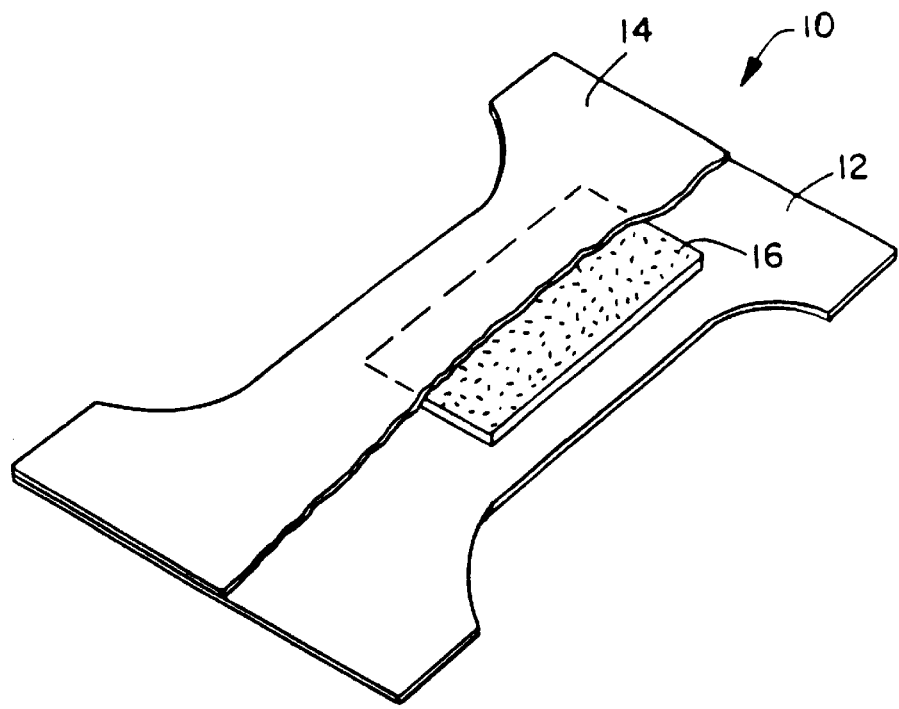
FIG. 1 shows a perspective view, partially in section, of a disposable diaper in accordance with the present invention.

The present invention includes an article and method for reducing malodor in disposable products for the absorption of body fluids. It has been found empirically that the article and method of the present invention including certain chemical treatments reduce odors associated with urine. In one aspect, the article and method of the present invention including certain chemical treatments reduce odors associated with urine when such treatments are applied to superabsorbent particles or composites. In one aspect, the article and method of the present invention including certain chemical treatments reduce odors associated with urine when such treatments are applied to wood pulp fluff. The certain chemical treatment for reducing odors associated with urine were found through the use of quantitative data obtained from reproducible test procedures.

Working chemical treatments were found in the form of treatments which did reduce odor in actual tests. Actual Examples tested the odor absorbing abilities of the treatments. I have found empirically that an absorbent product in accordance with the present invention containing xylitol forms an absorbent product effective in reducing urine odor.

In accordance with the present invention, an effective amount of a pentitol is applied to an absorbent material, prior to its use. In one aspect, an effective amount of a pentitol is applied to a water-swellable, water-insoluble, hydrogel-forming polymeric absorbent material, prior to its use. The pentitol is effective to reduce the odor of urine.

The pentitol, e.g., xylitol $C_5H_{12}O_5$, used in accordance with the present invention is the alcohol form of a pentose wood sugar, e.g., xylose $C_5H_{10}O_5$.

The xylitol used in accordance with the present invention has been classified as a polyol or a sugar alcohol and is referred to as birch sugar, because it can be produced from birch. Xylitol is a white crystalline powder and is made from acid-treated fibers of birch wood by a chemical process. The process requires high pressure and temperature, a catalyst, and extensive steps to remove byproducts.

Xylitol occurs widely in nature, although the concentrations are low. Natural sources of xylitol include plums, strawberries, raspberries, and rowan berries. Xylitol has the same relative sweetness as sucrose, and it has been used as a sugar substitute for dietary and medical purposes.

The pentitol used in accordance with the present invention may be formulated as a solid or liquid preparation. The solid preparation may be in the form of, for example, powder, and may contain conventional excipients and fillers. The liquid preparation may be in the form of, for example, an aqueous solution or syrup.

Pentitol is present in natural chemical cycles in the human body. It has about the same safety and toxicity as table sugar.

In one aspect, the present invention includes an article and method for reducing malodor in an absorbent structure having from about 10 to 100 weight percent, based on absorbent structure weight, of a water-swellable, water-insoluble, hydrogel-forming polymeric absorbent material. At least 2 percent of the absorbent bent material has a particle size of less than about 200 micrometers. A covering material at least partially covers an outer surface of the absorbent structure. Such absorbent products include diapers, training pants, adult incontinence products, feminine sanitary napkins, tampons, and the like.

For ease of understanding, the present invention will be explained in terms of an infant diaper, such as that illustrated in FIG. 1, and a disposable absorbent pad, such as that illustrated in FIG. 2. Nevertheless, it is understood that the invention is equally applicable to other absorbent products intended to absorb body fluids.

Referring now to FIG. 1, a disposable diaper 10 is illustrated. The disposable diaper 10 includes an outer covering material having a backing sheet 12 and a body-side liner 14. An absorbent structure 16 is located between the backing sheet 12 and the body-side liner 14. The absorbent structure 16 preferably has the construction of a fibrous matrix. The fibrous matrix preferably includes wood pulp fibers, synthetic polymeric fibers, or a combination of wood pulp fibers and synthetic polymeric fibers. In one embodiment, the absorbent structure 16 has from about 10 to 100 weight percent, preferably from about 30 to about 100 weight percent, and more preferably from about 40 to 75 weight percent, based on total absorbent structure weight, of a water-swellable, water-insoluble, hydrogel-forming polymeric absorbent material.

Figure 2:
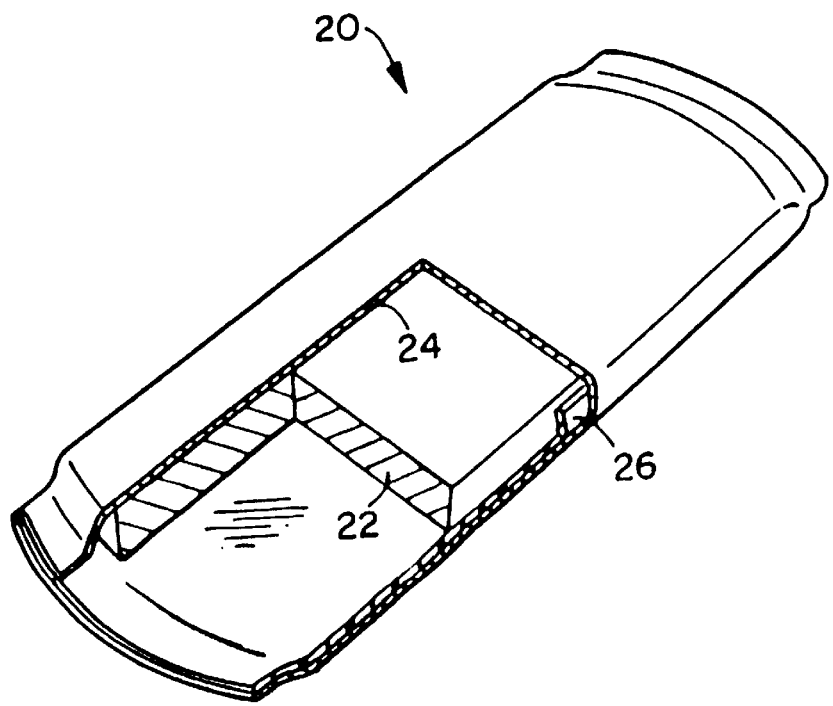
FIG. 2 shows a perspective view, partially in section, of a disposable absorbent pad in accordance with the present invention.

Referring now to FIG. 2, a disposable absorbent pad is illustrated according to the present invention. A disposable absorbent pad, such as, by way of example, feminine sanitary napkin 20 includes an absorbent structure 22, an outer covering 24, and a liquid-impervious baffle 26.

Such absorbent products include an absorbent structure and a covering layer which covers at least a portion of an outer surface of the absorbent structure. In the case of diapers, the covering layer includes a liquid-permeable body-side liner adapted to contact the skin of a wearer and a liquid-impervious outer cover. The absorbent structure is located between the body-side liner and the outer cover which may be joined along their periphery.

The absorbent structure may include a means for containing the superabsorbent material, such as a fibrous material, e.g., wood pulp fluff, synthetic polymeric fibers, or the like. Such fibers form a matrix in which the superabsorbent material may be contained. The means for containing the superabsorbent material includes a hydrophilic substrate. Other means for containing the superabsorbent material include foams, tissue, or laminates. When the absorbent structure includes about 100 weight percent superabsorbent, the superabsorbent may be contained, for example, in place between two flexible fiber sheets such as a tissue wrap sheet or nonwoven material.

Superabsorbent materials used in accordance with the present invention include water-swellable, water-insoluble, hydrogel-forming polymeric absorbent material superabsorbent capable of absorbing at least about 10, preferably about 20, and possibly about 100 times or more its weight in water. The hydrogel-forming polymeric absorbent material is formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers preferably are lightly cross-linked to render the material substantially water insoluble. Cross-linking may be by irradiation or covalent, ionic, Van der Waals, or hydrogen bonding. Suitable materials are available from various commercial vendors such as The Dow Chemical Company and Stockhausen, Inc.

Non-cellulosic synthetic hydrogel-forming polymers are formed through a suspension, including inverse suspension, or solution polymerization process. In a suspension polymerization process, monomeric material from which the absorbent material is to be formed is suspended in an inert medium and subsequently polymerized. In a solution polymerization process, the monomers from which the absorbent material is to be formed are dissolved in an aqueous phase and subsequently polymerized, dried, and ground into particles having a desired particle size range. In one preferred embodiment of the present invention, the non-cellulosic, synthetic hydrogel-forming polymers are preferred for use. Specifically, it is preferred that the absorbent material be selected from the group consisting of alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridines, hydrolyzed acrylonitrile grafted starch, acrylic acid grafted starch, and isobutylene maleic anhydride copolymers and mixtures thereof. It is preferred further that the synthetic hydrogel-forming polymers be formed through a solution polymerization process.

In accordance with the article and method of the present invention, there is applied to an absorbent product, prior to its use, an effective amount of a pentitol. The pentitol is effective to reduce the odor of urine.

As used herein, the term "pentitol" refers to a compound or mixture of compounds characterized by a 5 carbon linear chain sugar alcohol. The pentitols have the chemical formula $HOCH_2(CHOH)_3$—$CH_2OH$. The pentitols have 5 hydroxyl groups and include ribitol, D-arabinitol, L-arabinitol, and xylitol.

Xylitol provides a low cost, abundant source of pentitol.

The test method for determining whether or not pentitol reduced the odor of urine is set forth in connection with the actual Example which follows.

The pentitols in accordance with the article and method of the present invention do not deleteriously affect the absorbent product in which it is to be incorporated.

In one aspect, the pentitol is incorporated into the superabsorbent material during polymerization.

In one aspect, the superabsorbent material is coated with the pentitol after polymerization.

In one aspect, a solution containing the pentitol is sprayed directly on the absorbent hydrophilic-substrate structure.

In one aspect, inert particles are coated with the pentitol and incorporated in the absorbent hydrophilic-substrate structure.

In one aspect, the pentitol is applied as a coating on or incorporated into the body-side liner or cover of the diaper or absorbent pad.

In one aspect, the pentitol is applied as a coating on or incorporated into a surfactant applied to the body-side liner or cover of the diaper or absorbent pad.

The pentitol may be added to the superabsorbent material during polymerization.

In one aspect, the pentitol is provided in situ in the wood pulp fluff fiber. Pentitol reactive sites are provided in the wood fiber by modifying the wood fiber.

The pentitol preferably is located in the area of insult, i.e., that area of the absorbent product which is most likely to be exposed to the body fluid intended to be absorbed. In the case of a diaper, the pentitol is present in the front portion and crotch portion of the diaper.

Xylitols suitable for use in the present invention include a Xylitol available under the trademark XYLISORB® 90 available from Roquette America, Inc. in Keokuk, Iowa 52632.

The pentitol is applied to the absorbent products in an amount effective to reduce the odor of the absorbed body fluid. I have found that the odor-reduction capabilities with respect to urine of the xylitols are within certain limitations dependent on the amount of the xylitol present in the absorbent products. Relatively low levels of less than about 9 weight percent of the pentitol, based on total absorbent structure weight, are effective to reduce the odor associated with an absorbed body fluid.

By the term "absorbent structure weight" is meant any and all absorbent components, e.g., such as, wood pulp fluff, super-absorbent material, tissue, natural wood fibers, other natural fibers, synthetic fibers, or combinations of wood pulp fluff, superabsorbent material, tissue, natural wood fibers, other natural fibers, and synthetic fibers.

At relative concentrations of pentitol less than about 4 weight percent based on total weight of the absorbent structure, the malodor associated with the absorbent product is reduced to a much lesser extent. The amount of pentitol preferably present in the absorbent product depends, to a degree, on the amount of odor reduction desired. Any amount of pentitol effective to reduce perceptibly the odor associated with the used absorbent product is preferred for use in accordance with the article and method of the present invention.

The pentitol is present in the absorbent product in an amount of from about 1 to about 25 weight percent, based on total weight of the absorbent structure, preferably of from about 5 to about 20 weight percent, based on total weight of the absorbent structure, and more preferably of from about 7 to about 18 weight percent, based on total weight of the absorbent structure.

In one aspect, the absorbent body includes an absorbent structure having from about 10 to 100 weight percent, based on absorbent structure weight, of a solution polymerized, water-swellable, water-insoluble, hydrogel-forming polymeric absorbent material wherein at least about 2 weight percent of the absorbent material has a particle size of less than about 200 micrometers; and a covering material at least partially covering an outer surface of the absorbent structure; and an effective amount of a pentitol. The pentitol is effective to reduce the odor of urine.

EXAMPLE

The objective of the actual Example was to evaluate the post-use urine malodor of different absorbent incontinence products at 2, 5, and 8 hours following the addition of a predetermined amount of a pooled human urine specimen to the products.

Experimental design included product evaluation in a blinded, paired comparison test to determine comparative efficacy to control urine malodor after urine was introduced into the different absorbent incontinence products. Odor perception is, by its nature, a subjective olfactory determination. A Paired Comparison Protocol For Sensory Odor Screening Evaluation of Incontinence Products was used, which is described herein below. An adaptation of the methodology "Standard Practice For The Sensory Evaluation of Axillary Deodorancy (E 1207-87)," published by the American Society for Testing, and Materials, was used in the protocol.

Test articles were prepared by cutting a disposable absorbent article, peeling back the outer cover transfer layer and attached tissue to expose the fluff core. A chemical treatment was measured to the nearest 0.2 g and then uniformly added, i.e., evenly spread out, to the exposed fluff in the area of insult. The disposable absorbent article then was sealed with hook and loop type fastener. Control products were prepared in a similar appearance to make the test specimens visually indistinguishable.

The test articles were blind-coded with 3-digit random numbers. Treatment comparisons were as follows:

| Sample Comparison | Number of Replicates |
|---|---|
| Product 1 vs. Product 2 | 2 |

Urine collection was made by enlisting twenty female subjects sought to provide a urine specimen by 7:15 a.m. on the day of the test.

Each subject submitted her first morning urine in a clean specimen container to the laboratory by 7:15 a.m. on the day of the test. Healthy female subjects between the ages of 18 and 60 were solicited to provide urine for testing. Urine was not accepted from subjects who were menstruating, had any vaginal discharge, had a bladder infection, were pregnant or lactating, or had consumed asparagus, cabbage, cauliflower, broccoli, or eggs within the past twelve hours. All urine specimens were pooled in a 4000 ml glass beaker and mixed by placing a magnetic stirring rod in the beaker and placing the beaker on a stirring plate. Mixing was continued until all the test products have been inoculated with urine.

On the day of the test, the following test schedule routine was carried out on twelve (12) comparison pairs. Six trained odor judges were presented a pair of urine-inoculated products in individual containers in a randomized sequence and asked to rate "which test product in the pair has the highest urine malodor."

The test procedure used a test apparatus of clear glass containers with lids contain the urine-inoculated products. The container had a capacity to allow exposure of the wet surface of the product to the air inside.

For blind coding of the containers, each container was assigned a random three-digit number by the test coordinator.

For sample preparation, in groups of six at a time, the test products were placed flat on the lab bench where they were inoculated with a specified volume of pooled urine and allowed to rest for approximately 15 seconds to assure complete absorption. The inoculated products were placed in a "U" configuration inside a clear glass container. The wet surface of the product was exposed toward the center of the container, with the plastic backing of the product in contact with the glass surface of the container. An inverted Petri dish was placed over the container to serve as the lid.

Sixty (60) ml of urine was used per pad.

All containers remained closed and kept in a Blue M Oven set at 98° F.±2° F. until opened by a judge just prior to the odor evaluations.

For odor evaluations, each judge evaluated 2 pairs of test products at three test periods, 2, 5, and 8 hours after inoculation, to determine which test product in each pair had the highest urine malodor. The judges sniffed the head space in each container by opening the lid slightly, placing the nose just above the open area, and taking three to four small, quick inhalations. The lid was replaced on the container immediately after sniffing. A two minute delay was observed before the next container was opened. After the second product in a given pair was sniffed, the number of the one with the most urine malodor was recorded on a ballot by the judge. A sample ballot for the two hour comparison is as follows.

SAMPLE BALLOT

Name: _____  Date: _____

Study Number: _____  2 HOURS

Instructions:
1. Arrange jars in order from left to right.
2. Lift lid and smell product.
3. Replace lid.
4. Repeat procedure with second jar and product.
5. Choose the product that has the STRONGEST URINE/MALODOR.
6. Make an "X" on the appropriate line.
7. Open the door on the table in front of you, and push the covered jars through to the other side, when finished.

Station 1

Set 1.  191 _____  286 _____

Set 2.  311 _____  375 _____

The containers were returned to the Blue M Oven until the next evaluation period.

During the evaluation, each judge was isolated from the others in an individual booth in an evaluation room. The room was equipped with a positive air flow system to keep room air circulating and to prevent a buildup of odor.

For statistical analysis, data were analyzed by using a test of proportions methodology.

The paired comparison format was used to determine whether the intensity of urine malodor was significantly different for the test products.

Code D—Control, Extra absorbency DEPEND® pad (Europe)

Code L—Extra absorbency DEPEND® pad (Europe) with 1.5 g xylitol

Code H—Extra absorbency DEPEND® pad (Europe) with 3.0 g xylitol

The results are shown in Table 1. The summary gives the code pair being evaluated, the frequency that the first code listed in the pair was chosen as having a more intense urine malodor, the frequency that the second code listed in the pair was chosen as having a more intense urine malodor, the total number of times the pair was evaluated, the p-value for the comparison of the codes, and a column which is asterisked if the codes were significantly different in urine intensity at the 95% confidence level or above.

TABLE 1

| Pair | Freq 1$^{st}$ Code | Freq 2$^{nd}$ Code | Total | Prob | Sign |
|---|---|---|---|---|---|
| I. 2 hour evaluation | | | | | |
| D-L | 9 | 9 | 18 | 1.000 | |
| D-H | 11 | 7 | 18 | 0.349 | |
| II. 5 hour evaluation | | | | | |
| D-L | 12 | 6 | 18 | 0.165 | |
| D-H | 17 | 1 | 18 | 0.003 | ** |

TABLE 1-continued

| Pair | Freq 1st Code | Freq 2nd Code | Total | Prob | Sign |
|---|---|---|---|---|---|
| III. 8 hour evaluation | | | | | |
| D-L | 17 | 1 | 18 | 0.003 | ** |
| D-H | 18 | 0 | 18 | 0.000 | ** |

The results show that xylitol was effective in reducing urine malodor in pads inoculated with urine. Significant odor reduction was seen at 5 hours for the higher level of xylitol but not for the lower level. At 8 hours, both levels were effective at reducing odor.

The paired comparison format was used to determine whether the intensity of urine malodor was significantly different for the test products. Code P—Control, Extra absorbency POISE® pad Code M—Extra absorbency POISE® pad with 3.0 g xylitol The samples were tested at 2, 5, 8, and 24 hours. A total of six (6) panelists evaluated three replicates of all possible code pairs.

The results are shown in Table 2. The summary gives the code pair being evaluated, the frequency that the code listed was chosen as having a more intense urine malodor, and the total number of times the pair was evaluated.

TABLE 2

| ANSWER | Frequency | Percent | Cumulative Frequency | Cumulative Percent |
|---|---|---|---|---|
| I. 2 hour evaluation | | | | |
| M | 6 | 33.33 | 6 | 33.33 |
| P | 12 | 66.67 | 18 | 100.00 |
| II. 5 hour evaluation | | | | |
| M | 8 | 44.44 | 8 | 44.44 |
| P | 10 | 55.56 | 18 | 100.00 |
| III. 8 hour evaluation | | | | |
| M | 4 | 22.22 | 4 | 22.22 |
| P | 14 | 77.78 | 18 | 100.00 |
| IV. 24 hour evaluation | | | | |
| M | 5 | 27.78 | 5 | 27.78 |
| P | 13 | 72.22 | 18 | 100.00 |

The results show a significant difference between the codes for hour 8 (p-value=0.03 or 97% confidence level) and a significant/ marginal code difference for hour 24 (p-value= 0.07 or 93% confidence level). For both these time, frames code P (control no xylitol) was selected as having more intense urine malodor than code M (with 3.0 gram xylitol).

The article and method of the present invention are capable of modifications and variations without departing from the scope thereof. Accordingly, the detailed description and examples set forth above are meant to be illustrative only and are not intended to limit the scope of the invention as set forth in the appended claims.

What is claimed is:

1. A disposable absorbent product for absorbing a body fluid, comprising an absorbent structure and a xylitol present in an amount based on a weight percent of about 5 weight percent to about 20 weight percent of said absorbent structure weight.

2. The disposable absorbent product as set forth in claim 1, wherein said absorbent structure comprises a fibrous material.

3. The disposable absorbent product as set forth in claim 2, wherein said fibrous material is wood pulp fluff.

4. The disposable absorbent product as set forth in claim 2, wherein said absorbent structure comprises from about 10 to about 100 weight percent, based on total absorbent structure weight, of a hydrogel-forming polymeric superabsorbent material.

5. The disposable absorbent product as set forth in claim 2, wherein said absorbent structure is positioned within a covering material comprising a body-side liner and a backing sheet, said absorbent structure being located between said bodyside liner and said backing sheet.

6. The disposable absorbent product as set forth in claim 5, wherein said xylitol is coated on or incorporated into said body-side liner.

7. The disposable absorbent product as set forth in claim 2, wherein said xylitol is positioned inside said absorbent structure in that area of the absorbent product which is most likely to be exposed to the body fluid intended to be absorbed.

8. The disposable absorbent product as set forth in claim 2, wherein said xylitol is coated on said absorbent structure.

9. The disposable absorbent product as set forth in claim 1, wherein said xylitol is present in an amount based on a weight percent of about 7 weight percent to about 18 weight percent of said absorbent structure weight.

10. The disposable absorbent product as set forth in claim 1, wherein said xylitol is coated on said hydrogel-forming polymeric super absorbent material.

11. A method for reducing malodor in a disposable absorbent product for the absorption of body fluid, comprising a) providing an absorbent structure; and b) providing an odor reducing material added to said absorbent structure by providing pentitol applied to said absorbent product.

12. The method for reducing malodor in a disposable absorbent product for the absorption of body fluid as set forth in claim 11, wherein said absorbent structure comprises a fibrous material.

13. The method for reducing malodor in a disposable absorbent product for the absorption of body fluid as set forth in claim 12, wherein said fibrous material is wood pulp fluff.

14. The method for reducing malodor in a disposable absorbent product for the absorption of body fluid as set forth in claim 12, wherein said providing a pentitol comprises providing xylitol in an amount based on a weight percent in the range of about 5 weight percent to about 20 weight percent of said absorbent structure weight.

15. The method for reducing malodor in a disposable absorbent product for the absorption of body fluid as set forth in claim 12, wherein said providing an absorbent structure comprises providing from about 10 to about 100 weight percent, based on total absorbent structure weight, of a hydrogel-forming polymeric superabsorbent material.

16. The method for reducing malodor in a disposable absorbent product for the absorption of body fluid as set forth in claim 12, wherein said applying comprises applying said pentitol to said absorbent structure between a bodyside liner and a backing sheet.

17. The method for reducing malodor in a disposable absorbent product for the absorption of body fluid as set forth in claim 12, wherein said applying comprises coating pentitol on said absorbent structure.

18. The method for reducing malodor in a disposable absorbent product for the absorption of body fluid as set forth in claim 12, wherein said applying comprises applying said xylitol to said absorbent structure in the area of insult in the area of the absorbent product most likely to be exposed to the body fluid intended to be absorbed, wherein said absorbent structure is positioned within a covering material comprising a body-side liner and a backing sheet, said absorbent structure being located between said bodyside liner and said backing sheet.

19. A disposable absorbent product for absorbing a body fluid, comprising;

an absorbent structure comprising a fibrous wood pulp fluff and 20 to about 50 percent by weight, based on absorbent structure weight, of a hydrogel-forming polymeric absorbent material;

a covering material comprising a bodyside liner and a backing sheet, said covering material covering said absorbent structure, said absorbent structure being located between said bodyside liner and said backing sheet; and xylitol powder in said absorbent structure in an amount of about 7 weight percent to about 18 weight percent of said absorbent structure weight, wherein said xylitol is located in the area of the absorbent product to be exposed to the body fluid intended to be absorbed.

* * * * *